US012097352B2

(12) United States Patent
O'Connor et al.

(10) Patent No.: US 12,097,352 B2
(45) Date of Patent: Sep. 24, 2024

(54) WEARABLE MICRO-DOSING DRUG DELIVERY DEVICE

(71) Applicant: Insulet Corporation, Acton, MA (US)

(72) Inventors: Jason O'Connor, Acton, MA (US); Matthew Alles, Winchester, MA (US); Robert Sanzone, Sudbury, MA (US); Craig Brodeur, Marlborough, MA (US); Joseph Melo, Tewksbury, MA (US); Christopher Williams, Allston, MA (US); Noel Schaeffer, San Diego, CA (US)

(73) Assignee: INSULET CORPORATION, Acton, MA (US)

( * ) Notice: Subject to any disclaimer, the term of this patent is extended or adjusted under 35 U.S.C. 154(b) by 310 days.

(21) Appl. No.: 17/412,729

(22) Filed: Aug. 26, 2021

(65) Prior Publication Data

US 2022/0062536 A1    Mar. 3, 2022

Related U.S. Application Data

(60) Provisional application No. 63/150,871, filed on Feb. 18, 2021, provisional application No. 63/071,196, filed on Aug. 27, 2020.

(51) Int. Cl.
*A61M 5/142*    (2006.01)

(52) U.S. Cl.
CPC ............ *A61M 5/14244* (2013.01); *A61M 2005/14208* (2013.01); *A61M 2005/14252* (2013.01);
(Continued)

(58) Field of Classification Search
CPC ......... A61M 2005/14208; A61M 2005/14252; A61M 2205/18; A61M 2205/183;
(Continued)

(56) References Cited

U.S. PATENT DOCUMENTS

| 1,441,508 A | 1/1923 | Jensen |
| 2,897,214 A | 6/1961 | Radack |

(Continued)

FOREIGN PATENT DOCUMENTS

| EP | 3000497 A2 * | 3/2016 | ......... A61B 17/3403 |
| EP | 3135965 A1 | 3/2017 | |

(Continued)

OTHER PUBLICATIONS

International Preliminary Report on Patentability for the International Patent Application No. PCT/US2019/042160, mailed Jan. 28, 2021, 12 pages.

(Continued)

*Primary Examiner* — Quynh-Nhu H. Vu
(74) *Attorney, Agent, or Firm* — GOODWIN PROCTER LLP

(57) ABSTRACT

The disclosed embodiments are directed to a wearable automatic drug delivery device configured to provide basal-only dosing of insulin. In a primary embodiment, the wearable drug delivery device is configured to provide automatic operation and provides audible alerts and visual status indicators to the patient. In other embodiments, the patient may have some degree of control over the operation of the device by providing tapping gestures on housing of the device. In yet another embodiment, the patient may provide input and receive status from the device via an application executing on a portable computing device in wireless communication with the wearable drug delivery device.

34 Claims, 14 Drawing Sheets

(52) U.S. Cl.
CPC . *A61M 2205/18* (2013.01); *A61M 2205/3327* (2013.01); *A61M 2205/3553* (2013.01); *A61M 2205/50* (2013.01); *A61M 2205/581* (2013.01); *A61M 2205/584* (2013.01)

(58) Field of Classification Search
CPC ........ A61M 2205/50; A61M 2205/502; A61M 2205/581; A61M 2205/58; A61M 2205/583; A61M 2205/584; A61M 5/14244; A61M 5/14248
See application file for complete search history.

(56) References Cited

U.S. PATENT DOCUMENTS

| | | | |
|---|---|---|---|
| 3,579,805 A | 5/1971 | Kast | |
| 4,833,088 A | 5/1989 | Desimone et al. | |
| 5,232,668 A | 8/1993 | Grant et al. | |
| 5,244,459 A | 9/1993 | Hill | |
| 5,823,993 A * | 10/1998 | Lemelson | G01R 33/561 |
| | | | 604/21 |
| 5,920,263 A * | 7/1999 | Huttenhoff | G08B 7/06 |
| | | | 340/691.5 |
| 5,995,236 A | 11/1999 | Roth et al. | |
| 6,111,731 A * | 8/2000 | Cepynsky | H02H 7/0833 |
| | | | 307/107 |
| 6,142,181 A | 11/2000 | Schumacher | |
| 6,200,293 B1 | 3/2001 | Kriesel et al. | |
| 6,418,332 B1 | 7/2002 | Mastrototaro et al. | |
| 6,514,460 B1 | 2/2003 | Fendrock | |
| 6,740,059 B2 | 5/2004 | Flaherty | |
| 6,768,425 B2 | 7/2004 | Flaherty et al. | |
| 6,862,698 B1 * | 3/2005 | Shyu | G06F 11/079 |
| | | | 709/224 |
| 7,137,964 B2 | 11/2006 | Flaherty | |
| 7,303,549 B2 | 12/2007 | Flaherty et al. | |
| 7,731,900 B2 | 6/2010 | Haar et al. | |
| 7,842,241 B2 | 11/2010 | Arbogast et al. | |
| 7,846,385 B2 | 12/2010 | Arbogast et al. | |
| 7,846,386 B2 | 12/2010 | Arbogast et al. | |
| 7,846,387 B2 | 12/2010 | Arbogast et al. | |
| 7,846,388 B2 | 12/2010 | Arbogast et al. | |
| 7,867,446 B2 | 1/2011 | Arbogast et al. | |
| 7,897,107 B2 | 3/2011 | Arbogast et al. | |
| 7,914,742 B2 | 3/2011 | Arbogast et al. | |
| 8,003,052 B2 | 8/2011 | Sacherer | |
| 8,080,205 B2 | 12/2011 | Arbogast et al. | |
| D674,400 S | 1/2013 | Fong et al. | |
| D677,675 S | 3/2013 | Rampson et al. | |
| 8,431,408 B2 | 4/2013 | Lewis et al. | |
| D685,083 S | 6/2013 | Schneider et al. | |
| 8,465,977 B2 | 6/2013 | Joseph et al. | |
| D687,141 S | 7/2013 | Schneider et al. | |
| D687,536 S | 8/2013 | Guarraia et al. | |
| D688,681 S | 8/2013 | Talbot et al. | |
| D692,552 S | 10/2013 | Lovell et al. | |
| D703,690 S | 4/2014 | MacCubbin et al. | |
| 8,701,264 B2 | 4/2014 | Martinson | |
| 8,765,482 B2 | 7/2014 | Joseph et al. | |
| D713,854 S | 9/2014 | Cojuangco et al. | |
| D714,335 S | 9/2014 | Cojuangco et al. | |
| 8,894,262 B2 | 11/2014 | Celentano et al. | |
| D733,740 S | 7/2015 | Lee et al. | |
| D741,871 S | 10/2015 | Chung et al. | |
| 9,192,719 B2 * | 11/2015 | Rogers | A61M 5/14216 |
| D745,142 S | 12/2015 | OConnor et al. | |
| D748,664 S | 2/2016 | Noack et al. | |
| 9,265,877 B2 | 2/2016 | Mcarthur | |
| D752,607 S | 3/2016 | Zhang et al. | |
| D754,181 S | 4/2016 | Dong et al. | |
| D760,272 S | 6/2016 | Li | |
| D762,702 S | 8/2016 | Hoang et al. | |
| D764,507 S | 8/2016 | Gansca et al. | |
| D766,264 S | 9/2016 | Kahn et al. | |
| D768,188 S | 10/2016 | Li et al. | |
| D774,640 S | 12/2016 | Tyce et al. | |
| D776,262 S | 1/2017 | Tyce et al. | |
| D776,264 S | 1/2017 | Tyce et al. | |
| D776,265 S | 1/2017 | Tyce et al. | |
| D779,523 S | 2/2017 | Jensen et al. | |
| D779,526 S | 2/2017 | Volovik | |
| 9,572,926 B2 | 2/2017 | Cabiri | |
| D781,302 S | 3/2017 | Baguley et al. | |
| D784,395 S | 4/2017 | Laing et al. | |
| 9,633,497 B2 * | 4/2017 | Menzel | G06F 3/017 |
| D791,813 S | 7/2017 | Kisielius et al. | |
| D794,776 S | 8/2017 | Tyce et al. | |
| D795,272 S | 8/2017 | Laing et al. | |
| D802,011 S | 11/2017 | Friedman et al. | |
| D804,019 S | 11/2017 | Costello et al. | |
| 9,814,832 B2 | 11/2017 | Agard et al. | |
| D804,650 S | 12/2017 | Costello et al. | |
| D805,186 S | 12/2017 | Costello et al. | |
| D805,187 S | 12/2017 | Costello et al. | |
| D805,188 S | 12/2017 | Costello et al. | |
| D805,189 S | 12/2017 | Costello et al. | |
| D805,190 S | 12/2017 | Costello et al. | |
| D807,389 S | 1/2018 | Miller et al. | |
| D810,122 S | 2/2018 | McClellan | |
| D810,278 S | 2/2018 | Cabiri et al. | |
| D813,380 S | 3/2018 | Stonecipher et al. | |
| D816,092 S | 4/2018 | Mazur et al. | |
| D816,698 S | 5/2018 | Oldenburger et al. | |
| D817,481 S | 5/2018 | Cabiri et al. | |
| D817,977 S | 5/2018 | Kato et al. | |
| D822,692 S | 7/2018 | Loychik et al. | |
| D824,933 S | 8/2018 | Harris et al. | |
| D826,239 S | 8/2018 | Duriseti et al. | |
| D826,956 S | 8/2018 | Pillalamarri et al. | |
| D829,229 S | 9/2018 | Durkan et al. | |
| RE47,100 E | 10/2018 | Smith et al. | |
| D830,407 S | 10/2018 | Kisielius et al. | |
| D831,034 S | 10/2018 | Hoang et al. | |
| D833,461 S | 11/2018 | Dieken et al. | |
| D834,061 S | 11/2018 | Wall et al. | |
| D834,610 S | 11/2018 | Kim | |
| D835,116 S | 12/2018 | Taylor et al. | |
| D835,631 S | 12/2018 | Yepez et al. | |
| D835,663 S | 12/2018 | Ho et al. | |
| D836,770 S | 12/2018 | Nazzaro et al. | |
| D837,240 S | 1/2019 | Van Tricht | |
| D838,359 S | 1/2019 | Boyaval et al. | |
| D838,840 S | 1/2019 | Cabiri et al. | |
| D839,284 S | 1/2019 | Pillalamarri et al. | |
| D840,420 S | 2/2019 | Chalker et al. | |
| D840,421 S | 2/2019 | Chalker et al. | |
| D840,531 S | 2/2019 | Guillermo et al. | |
| D841,023 S | 2/2019 | Millett | |
| D844,652 S | 4/2019 | Edman | |
| D845,991 S | 4/2019 | Kessler et al. | |
| D847,154 S | 4/2019 | Cheney et al. | |
| D847,852 S | 5/2019 | Sapre | |
| D848,460 S | 5/2019 | Wiese et al. | |
| D849,767 S | 5/2019 | Mok et al. | |
| D851,666 S | 6/2019 | Lu et al. | |
| D851,752 S | 6/2019 | Nazzaro et al. | |
| D853,416 S | 7/2019 | Ryan et al. | |
| D853,426 S | 7/2019 | Alexander | |
| D853,427 S | 7/2019 | Alexander | |
| D854,559 S | 7/2019 | Dudey | |
| D856,506 S | 8/2019 | Wu et al. | |
| 10,549,051 B2 * | 2/2020 | Rosinko | A61M 5/5086 |
| 10,661,012 B2 | 5/2020 | Nazzaro et al. | |
| 11,039,491 B2 * | 6/2021 | Zheng | A61M 5/1723 |
| 11,511,037 B2 * | 11/2022 | Deliwala | A61B 5/0538 |
| 2004/0116847 A1 | 6/2004 | Wall | |
| 2005/0009126 A1 | 1/2005 | Andrews et al. | |
| 2005/0125162 A1 | 6/2005 | Hajizadeh et al. | |
| 2005/0201897 A1 | 9/2005 | Zimmer et al. | |
| 2005/0232815 A1 | 10/2005 | Ruhl et al. | |
| 2005/0238507 A1 | 10/2005 | Dilanni et al. | |
| 2005/0277164 A1 | 12/2005 | Drucker et al. | |
| 2009/0204078 A1 | 8/2009 | Mitchell et al. | |
| 2009/0254041 A1 | 10/2009 | Krag et al. | |

(56) References Cited

U.S. PATENT DOCUMENTS

| | | |
|---|---|---|
| 2009/0282947 A1 | 11/2009 | Powell |
| 2010/0152658 A1 | 6/2010 | Hanson et al. |
| 2010/0168683 A1 | 7/2010 | Cabiri |
| 2010/0317951 A1 | 12/2010 | Rutkowski et al. |
| 2011/0071765 A1 | 3/2011 | Yodfat et al. |
| 2011/0193704 A1 | 8/2011 | Harper et al. |
| 2011/0218495 A1 | 9/2011 | Remde |
| 2011/0289497 A1 | 11/2011 | Kiaie et al. |
| 2011/0306931 A1* | 12/2011 | Kamen ............ A61B 5/15186 604/93.01 |
| 2012/0095316 A1 | 4/2012 | Lewis et al. |
| 2012/0201048 A1 | 8/2012 | Prais |
| 2013/0204130 A1 | 8/2013 | McArthur et al. |
| 2014/0012119 A1 | 1/2014 | Geaghan et al. |
| 2014/0054883 A1 | 2/2014 | Lanigan et al. |
| 2014/0074033 A1 | 3/2014 | Sonderegger et al. |
| 2014/0078263 A1 | 3/2014 | Kim |
| 2014/0131199 A1 | 5/2014 | Simmons et al. |
| 2014/0148784 A1 | 5/2014 | Anderson et al. |
| 2014/0254170 A1 | 9/2014 | Celentano et al. |
| 2014/0296787 A1 | 10/2014 | Agard et al. |
| 2014/0316379 A1 | 10/2014 | Sonderegger et al. |
| 2015/0283335 A1 | 10/2015 | Lin |
| 2015/0338349 A1 | 11/2015 | Carter et al. |
| 2015/0361154 A1 | 12/2015 | Jowett et al. |
| 2015/0366945 A1 | 12/2015 | Greene |
| 2016/0015891 A1 | 1/2016 | Papiorek |
| 2016/0038689 A1 | 2/2016 | Lee et al. |
| 2016/0058941 A1 | 3/2016 | Wu et al. |
| 2016/0135747 A1 | 5/2016 | Frey et al. |
| 2016/0296699 A1* | 10/2016 | Cabiri ..................... A61M 5/20 |
| 2016/0310665 A1 | 10/2016 | Hwang et al. |
| 2017/0028132 A1 | 2/2017 | Cronenberg et al. |
| 2017/0106138 A1 | 4/2017 | Cabiri |
| 2017/0189270 A1 | 7/2017 | Nazzaro et al. |
| 2017/0214584 A1 | 7/2017 | Kanojia et al. |
| 2017/0234858 A1 | 8/2017 | Depa et al. |
| 2017/0348479 A1 | 12/2017 | Choate et al. |
| 2017/0354785 A1 | 12/2017 | Gazeley et al. |
| 2018/0015274 A1 | 1/2018 | Haury et al. |
| 2018/0075200 A1 | 3/2018 | Davis et al. |
| 2018/0207357 A1 | 7/2018 | John |
| 2018/0236173 A1 | 8/2018 | Mccaffrey et al. |
| 2018/0256815 A1 | 9/2018 | Nazzaro |
| 2018/0307515 A1 | 10/2018 | Meller et al. |
| 2019/0022317 A1* | 1/2019 | Uddin ............... A61M 5/14244 |
| 2019/0091404 A1 | 3/2019 | Nazzaro et al. |
| 2019/0132801 A1 | 5/2019 | Kamath et al. |
| 2019/0167895 A1 | 6/2019 | Dechellette et al. |
| 2019/0197895 A1 | 6/2019 | OSullivan |
| 2019/0240417 A1 | 8/2019 | Hostettler et al. |
| 2019/0321545 A1 | 10/2019 | Saint |
| 2020/0197605 A1 | 6/2020 | Haidar |
| 2020/0261643 A1 | 8/2020 | Boyaval et al. |
| 2021/0128831 A1* | 5/2021 | Zade ..................... G16H 40/67 |
| 2023/0330328 A1* | 10/2023 | Moberg ................. A61M 5/24 |

FOREIGN PATENT DOCUMENTS

| | | | |
|---|---|---|---|
| EP | 3000497 A1 | 1/2019 | |
| FR | 2096275 A5 | 2/1972 | |
| GB | 357139 A | 9/1931 | |
| GB | 810488 A | 3/1959 | |
| JP | 2009523535 A | 6/2009 | |
| JP | 2019525276 A | 9/2019 | |
| WO | 2007084214 A1 | 7/2007 | |
| WO | WO-2007092618 A2 * | 8/2007 | ........... A61B 5/0024 |
| WO | 2017091624 A1 | 6/2017 | |
| WO | 2019195521 A1 | 10/2019 | |
| WO | 2019213493 A1 | 11/2019 | |
| WO | 2019246381 A1 | 12/2019 | |
| WO | 2021011738 A1 | 1/2021 | |

OTHER PUBLICATIONS

International Search Report and Written Opinion for the International Patent Application No. PCT/US2021/047695, mailed Jan. 31, 2022, 26 pages.

International Search Report and Written Opinion for the International Patent Application No. PCT/US21/064056, mailed Apr. 4, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/blob/199ef86a900adf4b3d9c32f605eb11047bd3d62f/docs/EN/Module/module.rst [retrieved on Apr. 11, 2022] the whole document.

International Search Report and Written Opinion for the International Patent Application No. PCT/US22/018700, mailed Jun. 7, 2022, 13 pages.

Legacy Med Search, Insulet Enrolls First Patients in Clinical Trial for Omnipod, Sep. 16, 16, available at URL: https://legacymedsearch.com/insulet-enrolls-first-patients-in-clinical trial-for-omnipod-artificial-pancreas-system/.

International Preliminary Report on Patentability in PCT/US2021/047695 mailed on Mar. 9, 2023, 17 pages.

* cited by examiner

WEARABLE MICRO-DOSING DRUG DELIVERY DEVICE

CROSS REFERENCE TO RELATED APPLICATIONS

This application claims the benefit of U.S. Provisional Application Ser. No. 63/150,871, filed Feb. 18, 2021 and U.S. Provisional Application Ser. No. 63/071,196, filed Aug. 27, 2020, the contents of which are incorporated herein by reference in their entirety. Additionally, the contents of U.S. Provisional Application Ser. No. 63/072,417, filed Aug. 31, 2020, are incorporated herein by reference in their entirety.

BACKGROUND

Many individuals require medications delivered in micro-dose quantities. For example, diabetics require daily basal doses of insulin or a coformulation of insulin and GLP-1 to be delivered in micro-doses over the course of a day. Likewise, chemotherapy drugs, fertility drugs and other drugs, such as methadone are sometimes required to be delivered in micro-dose quantities.

Many individuals suffering from Type 2 diabetes require a basal level of insulin on a daily basis. For these individuals, delivery of the basal insulin may be accomplished via a daily shot of long-acting insulin. Often, however, Type 2 individuals may struggle to adhere to a regimen of antidiabetic drugs delivered via injection for a variety of reasons, including, for example, fear of self-administration of the injections, inconvenience, poor patient-physician communications and negative patient perceptions of both the drug and the procedure.

A number of wearable drug delivery devices provide delivery of drugs, such as insulin (both rapid-acting and long-acting), GLP-1, chemotherapy drugs, pain management drugs and the like. An example of one such drug delivery device is the OmniPod® drug delivery device manufactured by Insulet Corporation of Acton, Massachusetts, shown as reference number 100 in FIG. 1, or devices such as those described in U.S. Pat. Nos. 7,303,549, 7,137, 964 or 6,740,059, each of which is incorporated herein by reference in its entirety. However, known devices are designed to deliver bolus doses of insulin to supplement basal doses which are self-administered by the patient via a daily shot. Therefore, a need exists for a simple, wearable device that provides basal dosing of insulin with minimal input from or interaction with the patient to promote patient adherence with the drug regimen.

DEFINITIONS

As used herein, the term "liquid drug" is defined to include rapid-acting and long-acting insulin, GLP-1, coformulations of GLP-1 and long-acting or rapid-acting insulin, chemotherapy drugs, pain relief drugs (e.g., morphine), blood pressure medications, hormones, methadone, and any other single drug or combination thereof to be administered in liquid form.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is a wearable drug delivery device, referred to herein as a "basal pod", for delivering a basal-only dose of a liquid drug to a patient, and not delivery of bolus dose(s) of liquid drug to a patient. A single basal pod, when worn by the patient, is designed to deliver small doses of the liquid drug to the patient continuously over a period of several days, after which the basal pod will be removed from the patient's body and either replaced with a new basal pod or re-filled and re-used. The basal pod is designed to operate autonomously, with little or no interaction with the patient after application to the patient's body.

In preferred embodiments, the basal pod is filled with rapid-acting insulin which is delivered to the patient over the course of 72 hours.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

The invention is explained herein in terms of its use by persons suffering from Type II diabetes who require daily basal doses of insulin. However, as would be realized by one of skill in the art, the invention may be used by any person requiring micro-dosing of a liquid drug, as defined herein.

Devices and methods in accordance with the present disclosure will now be described more fully hereinafter with reference to the accompanying drawings, where one or more embodiments are shown. The devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the devices and methods disclosed herein provides one or more advantages over conventional systems, components, and methods.

Figure 2:
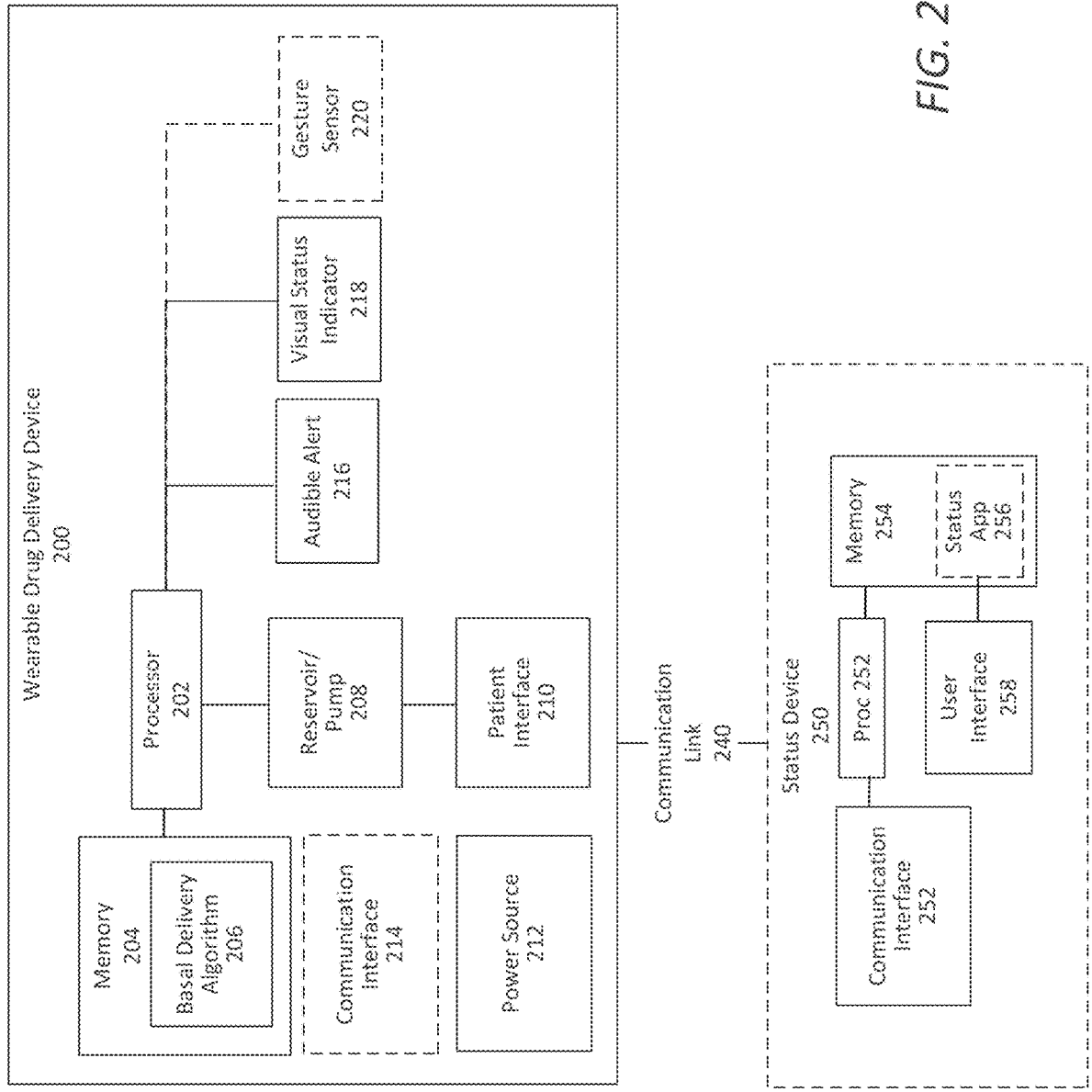
FIG. 2 block diagram showing various components of several different embodiments of the invention.

FIG. 2 illustrates a functional block diagram of an exemplary drug delivery device 200 in accordance with the present invention and suitable for providing a basal-only dose of a liquid drug over a period of several days. In exemplary embodiments, drug delivery device 200 is configured to not deliver bolus doses to a patient over the period of several days and accordingly is not configured with bolus buttons or bolus functionality.

The drug delivery device 200 may implement (and/or provide functionality for) a basal delivery algorithm 206 to govern or control automated delivery of the basal doses of the liquid drug without any user interaction, or in some examples, limited user interaction.

Figure 1:
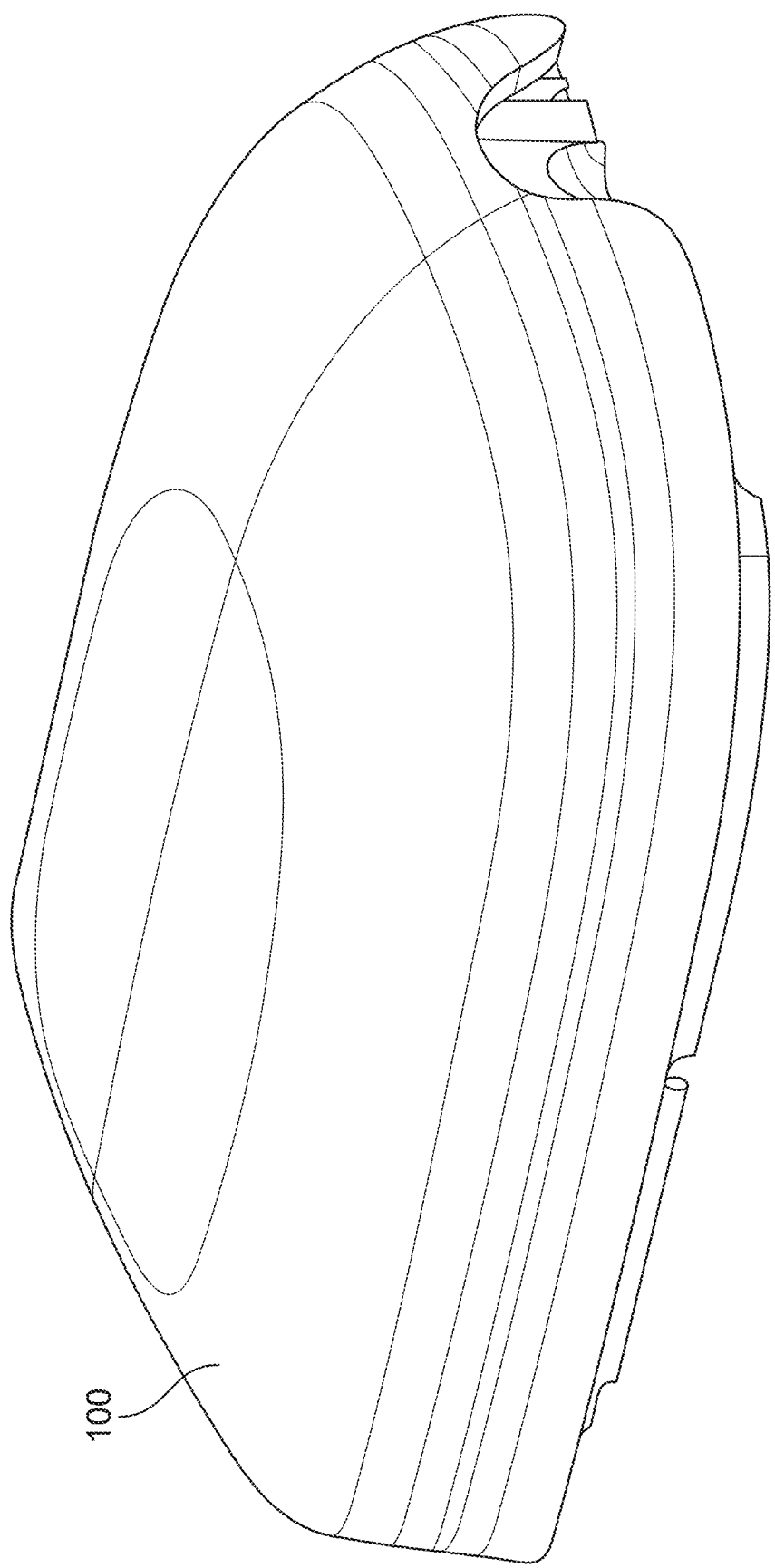
FIG. 1 is an illustration of a prior art wearable drug delivery device.

The basal pod 200 may be housed in housing 100 similar to that shown in FIG. 1 for prior art wearable drug delivery devices. Housing 100 may be a single piece or multiple pieces joined together and may come preconfigured with an adhesive on a bottom surface thereof to facilitate attachment of the basal pod 200 to the skin of the patient.

The basal pod 200 may be configured with a processor 202 which executes software or programming code stored in the memory 204, such as basal delivery algorithm 206. The basal delivery algorithm 206 may be an application operable to cause the basal pod 202 to deliver basal doses of the liquid drug in accordance with pre-programmed parameters.

Processor 202 may control a reservoir and pump 208 which is configured to pump the liquid drug from a reservoir to patient interface 210 in pre-configured doses. In some embodiments, the reservoir and pump may be integrated into a single unit, while in other embodiments, the reservoir and pump may be separate units wherein the pump is configured to draw the liquid drug from reservoir 208 and deliver it to patient interface 210.

Patient interface 210 may comprise a needle or cannula for delivering the drug into the body of the patient (which may be done subcutaneously, intraperitoneally, or intravenously). Processor 202 may control patient interface 210 such as to cause the patient interface 210 to be inserted into the body of the patient after the basal pod 200 has been attached to the body of the patient. Programmable code for controlling the insertion of the patient interface 210 may be stored in memory 204 and executed by processor 202 and may be part of or separate from basal delivery algorithm 206.

In some embodiments, the basal pod 200 may be configured with an audible alert 216 which is used as explained below. Audible alert 216 may comprise, for example, a piezoelectric audio transducer or a speaker. The basal pod 200 may also be configured with a visual status indicator 218 which may be, for example, a multi-colored LED, the use and purpose of which is also explained below.

In some embodiments, the basal pod 200 may include a communication interface 214 which may be a wireless transceiver that operates according to one or more radio-frequency protocols, such as Bluetooth, Wi-Fi, a near-field communication standard, a cellular standard, or the like.

In some embodiments, the basal pod 200 may optionally communicate, via communication interface 214, with a status device 250. Status device 250 may be configured with a processor 252 and a memory 254 containing a status application 256. The status application 256 may be configured to provide the patient with status information regarding the basal pod 200 via a user interface 258 and may allow some degree of control over the operation of device 200. Status may be received by status device 250 via communication interface 252 which may communicate with communication interface 214 on the basal pod 200 via communication link 240. In some embodiments, status device 250 may comprise, for example, a smartphone, a tablet device, a smartwatch, or any other personal mobile computing device capable of running status application 256 and receiving status from the basal pod 200 via communication link 240. In some embodiments, for example, in a hospital setting, the status device 250 may be a hub connecting a plurality of basal pods 200 from a plurality of patients, such that the plurality of patients could be simultaneously monitored at a single location.

The basal pod 200, including all components previously discussed, are powered by power source 212, which may be, for example, one or more batteries or a power harvesting apparatus.

Figure 3A:
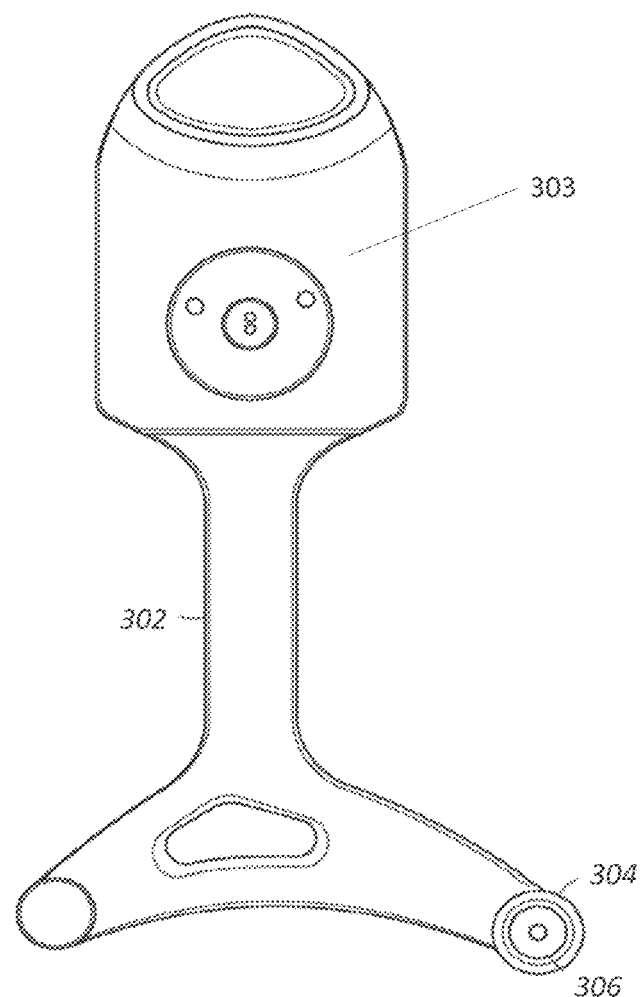
FIG. 3A illustrates one possible embodiment of the wearable drug delivery device providing a syringe and needle guide for the fill port of the device.
Figure 3B:
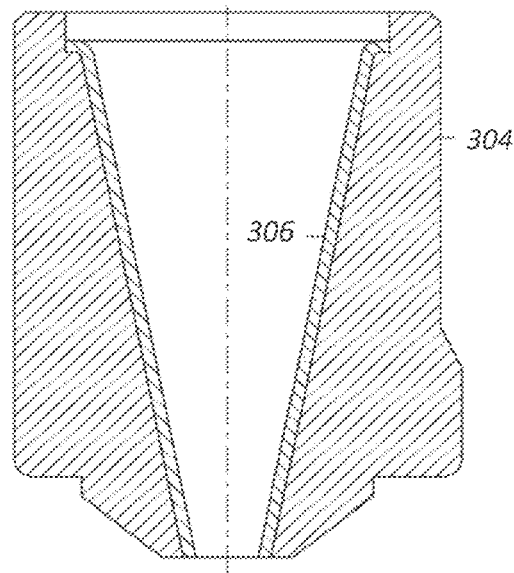
FIG. 3B is a cross sectional view of the needle guide.

The basal pod 200 may be provided with a removable cap 302 shown in FIG. 3A on the bottom surface thereof. Cap 302 serves several purposes. First, area 303 of cap 302 covers the opening in the housing 100 of the basal pod 200 through which the cannula is deployed to protect the needle and cannula during shipping of the device 200. Second, cap 302 provides a guide 304 positioned over a fill port 404 (See FIG. 4C) of device 200. Guide 304 serves to assist the patient in the proper alignment of the needle of a syringe as it is inserted in fill port 404 to fill reservoir 208 of device 200 with the liquid drug. In addition, guide 304 may serve to prevent the user from inserting the needle too far into device 200, which may damage device 200. FIG. 3B shows one embodiment of guide 304 in a cross-sectional view, which shows guide 304 having an internal, tapered conical surface which tends to guide the needle of a syringe toward fill port 404. Various alternate embodiments of cap 302 are shown in U.S. Pat. No. 10,661,012, the contents of which are incorporated herein in their entirety.

In operation, processor 202 of the basal pod 200 executes the basal delivery algorithm. Initially, processor 202, under the direction of the basal delivery algorithm 206 is in communication with patient interface 210 to cause the cannula to be inserted into the skin of the patient. Once the patient interface has been correctly deployed, basal delivery algorithm 206 will determine the timing and size of the basal doses of the liquid drug to be dispensed from reservoir/pump 208 via patient interface 210 under control of processor 202. The size and timing of the basal delivery dosage may be dependent upon preprogrammed parameters. When basal delivery algorithm 206 determines it is time for the next dose of the liquid drug, processor 202 instructs reservoir pump 208 to expel the required quantity of the liquid drug from the reservoir pump to the patient via patient interface 210.

A first, primary embodiment of the invention is designed to provide the patient with the simplest possible experience in the use of the basal pod. The basal pod 200 will have pre-programmed basal rates. For example, in some embodiments, the pre-programmed basal rates could include 10 u, 15 u, 20 u, 30 u, 35 u, 40 u per day. As would be realized by one of skill in the art, any pre-programmed basal rate could be made available. Should a health care provider determine that the patient requires different basal rates, in one embodiment, the patient would be required to switch to a different model of the basal pod 200 having a different pre-programmed basal rate. In addition, the basal pod 200, under control of the basal delivery algorithm 206, provides a timed, automatic deployment of the cannula. Status of the device is conveyed to the patient via a visible status indicator, preferably, an LED contained within and visible through the housing 100 of the device. In addition, alert conditions of the basal pod 200 may be conveyed to the user via an audible alert. In this embodiment of the invention, no status device 250 is used and, as such, the basal pod 200 may not be configured with communication interface 214, or, alternatively, communication interface 214 may be disabled.

As such, drug delivery device may be less expensive than prior art devices in that fewer components may be required.

As mentioned above, each drug delivery device 200 may have a different pre-programmed basal rate. In an exemplary embodiment, drug delivery devices may be color-coded and/or number-coded based on their pre-programmed basal rate. For example, a drug delivery device 200 that is pre-programmed to deliver 40 units of basal insulin over a 24-hour period may be colored blue and/or be labeled on the housing, for example, with a label such as "Basal 40 U." And a drug delivery device that is pre-programmed to delivery 20 units of basal insulin over a 24-hour period may be colored green and/or labeled on the housing, for example, with a label such as "Basal 20 U." The amount of insulin pre-programmed to be delivered via basal delivery over a 24-hour period may vary based on different users, for example, children or adults, or based on the severity of the patient's pathology, and the user may readily know, based on the color coding, the indication of "Basal," and/or a label of the number of units, for example, which drug delivery device is appropriate for their situation.

Figure 7:
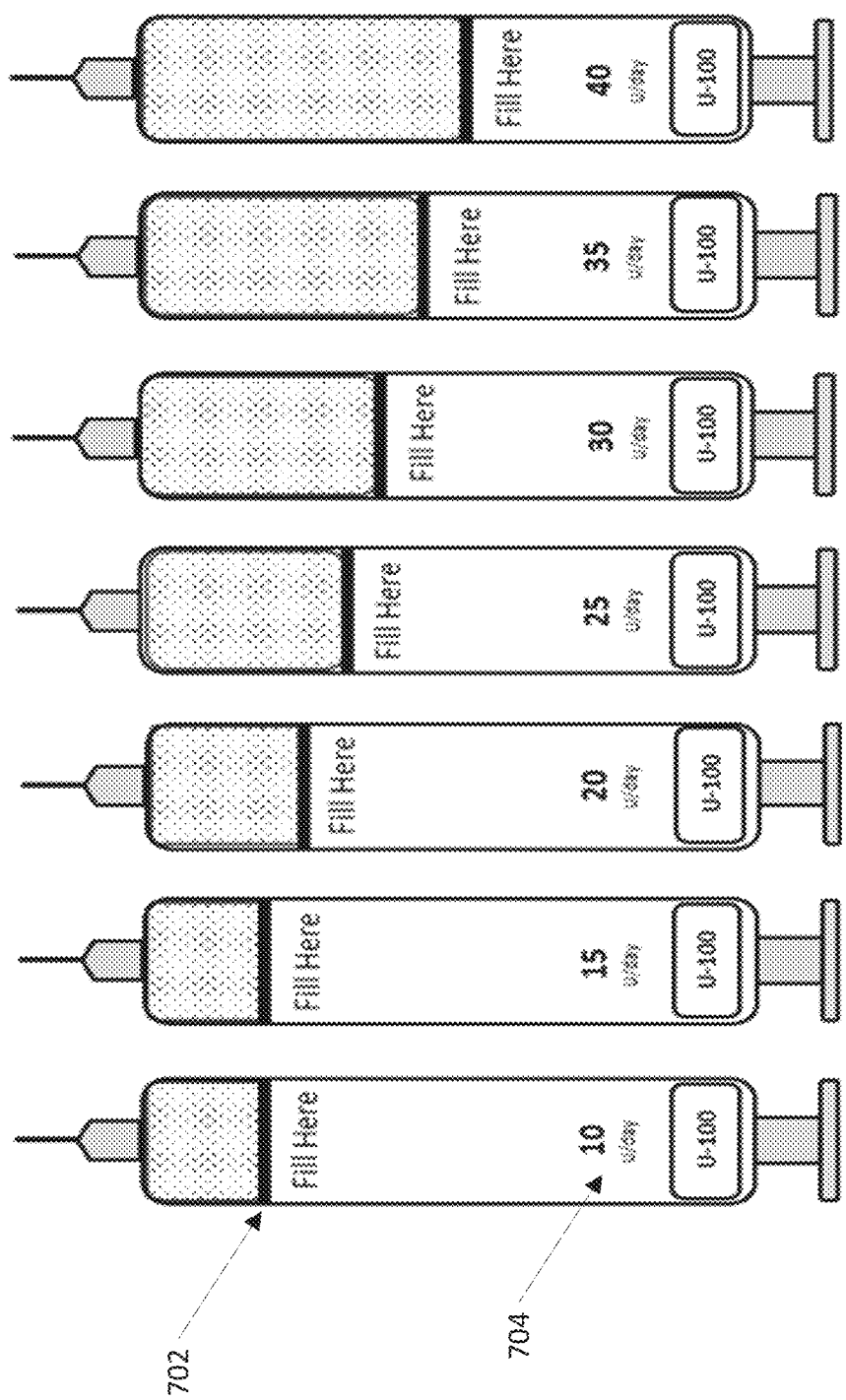
FIG. 7 shows a variety of syringes which may be used to assist users in filling the devices with the liquid drug having markings specific to devices with various pre-programmed basal rates.

In certain embodiments, each drug delivery device 200 may be sold accompanied by a syringe which may be used to fill the drug delivery device with the liquid drug. As shown in FIG. 7, the accompanying syringe may have a line 702 indicating the quantity of liquid drug to be extracted from a vial and inserted into drug delivery device 200. In addition, the syringe may be marked with the basal rate 704. The basal rate 704 may be color-coded to match the label on drug delivery device 200 which, as previously discussed, may also be color-coded with different colors indicating different pre-programmed basal rates.

In certain embodiments, and, in particular for new users of the device, a starter kit may be provided which may include several drug delivery devices having different pre-programmed basal rates, along with accompanying pre-labeled and color-coded syringes to be used for filling the devices. For example, in one embodiment, the starter kit may be outfitted with five 10-unit devices, five 15-unit devices and five 20-unit devices. Other arrangements of devices having quantities of devices and different pre-programmed basal rates may be used. Also included in the starter kit may be, for example, a quick start guide and instructional training materials, such as a user guide.

Figure 4A:
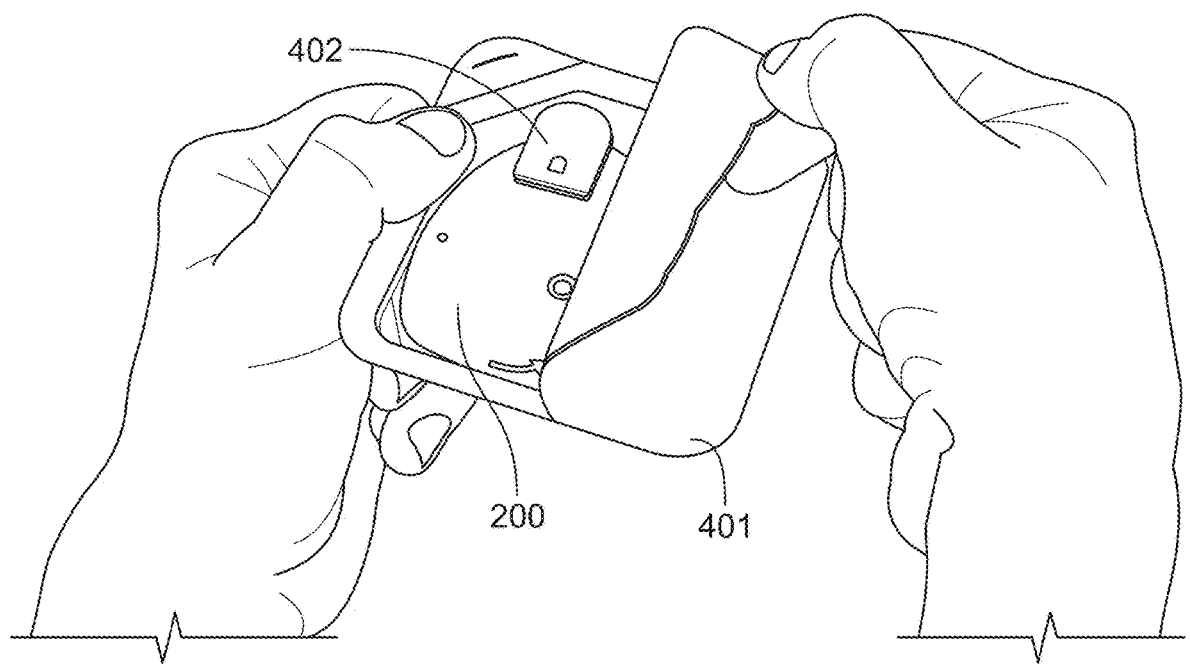
FIGS. 4A-4L show various steps in the operation of a first embodiment of the device, showing the novel features of the embodiments.

FIGS. 4A-4L show operation of a first, primary embodiment of the basal pod 200. Disposable versions of basal pod 200 may come prepackaged in sealed containers 401 as shown in FIG. 4A. As previously stated, various models of the basal pod 200 may come with different pre-programmed basal rates such that the patient may choose the proper model of the basal pod 200 based upon the desired basal rate as prescribed by the patient's healthcare professional. In a first step, the patient removes the basal pod 200 from the sealed container 401. Note that in the embodiment shown in FIG. 4A, basal pod 200 is provided with cap 402 which serves to cover the opening through which the cannula will be deployed. In various aspects of embodiments of the invention, basal pod 200 may be provided with the cap shown in FIGS. 3(A-B) and discussed above, which may also include the fill port guide 304 to assist the user in filling the basal pod 200 with the liquid drug, or with the cap 402 shown in FIG. 4.

Figure 4B:
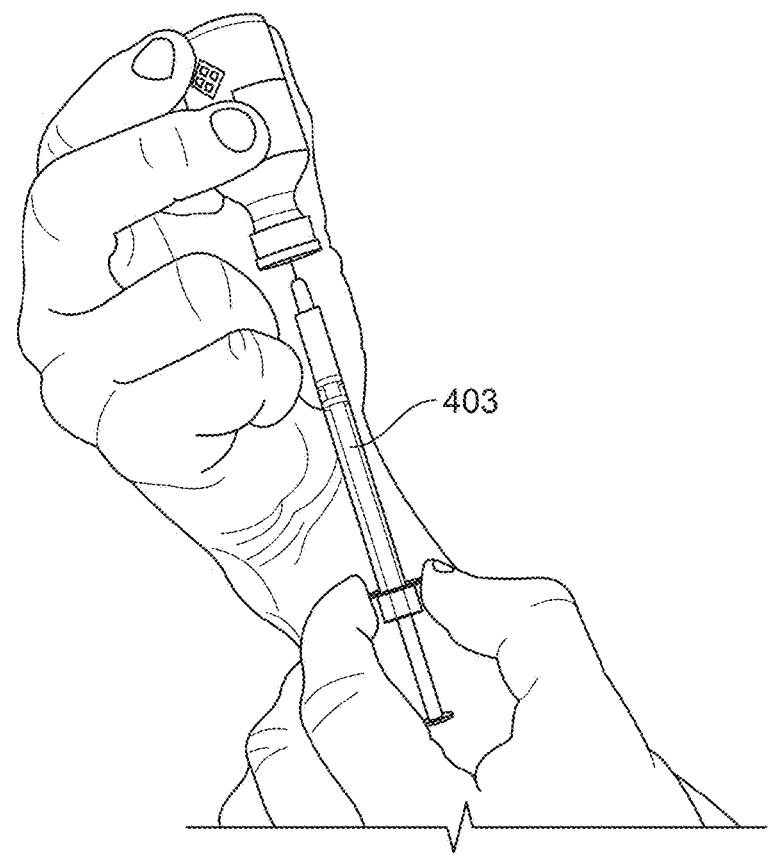
Figure 4C:
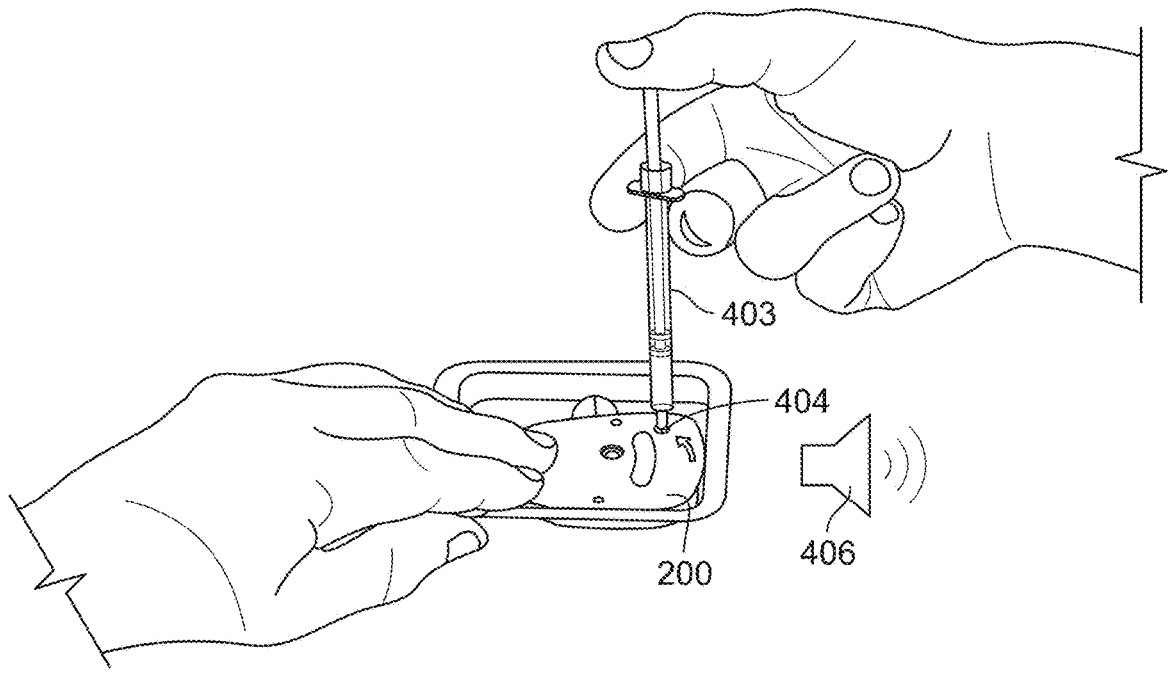

In FIG. 4B, the patient fills a syringe 403 with the liquid drug from a container of the liquid drug. Preferably syringe 403 will have a single fill line to avoid ambiguity and errors in drawing the proper amount of the liquid drug from the container. In a preferred embodiment of the invention, the liquid drug is a rapid acting insulin. FIG. 4C shows the patient inserting the needle of the syringe 403 into the fill port 404 of the basal pod 200. As the needle of the syringe 403 is inserted into the fill port 404, it may pierce a septum positioned in fill port 404. As previously noted, in other aspects of the invention, the patient may insert the needle of the syringe 403 into the fill port guide 304 of the cap 302 to assist the user in proper alignment of the syringe 403 with the fill port 404 of the basal pod 200. As the patient depresses the plunger of syringe 403, the liquid drug is transferred from the syringe 403 through the fill port 404 of the basal pod 200 and into reservoir 208. In other embodiments of the invention, basal pod 200 may come pre-filled with the liquid drug.

Basal delivery algorithm 206 is able to detect that the liquid drug has been inserted into reservoir 208. This detection may be based on input from a sensor (not shown) which senses, for example, the position of a plunger within the reservoir 208. Any other means known in the art for detecting that the liquid drug has been deployed in reservoir 208 is also intended to be within the scope of the invention. Insertion of the liquid drug into reservoir 208 may begin a timer which, when expired, will initiate the automatic deployment of the cannula (not shown) into the skin of the patient. In preferred embodiments of the invention, the timer may be set to a period of time at least long enough for the patient to position the basal pod 200 on his or her body, for example, three minutes. Optionally, basal pod 200 may activate an audible alert 216 to emit one or more beeps to alert the patient that the timer has been initiated, indicating that the patient should proceed with the positioning of the basal pod 200 on his or her body. In other embodiments, for example wherein the basal pod 200 comes pre-filled with the liquid drug, the timer may be initiated using another mechanism, for example, removal of cap 302 or 402.

Figure 4D:
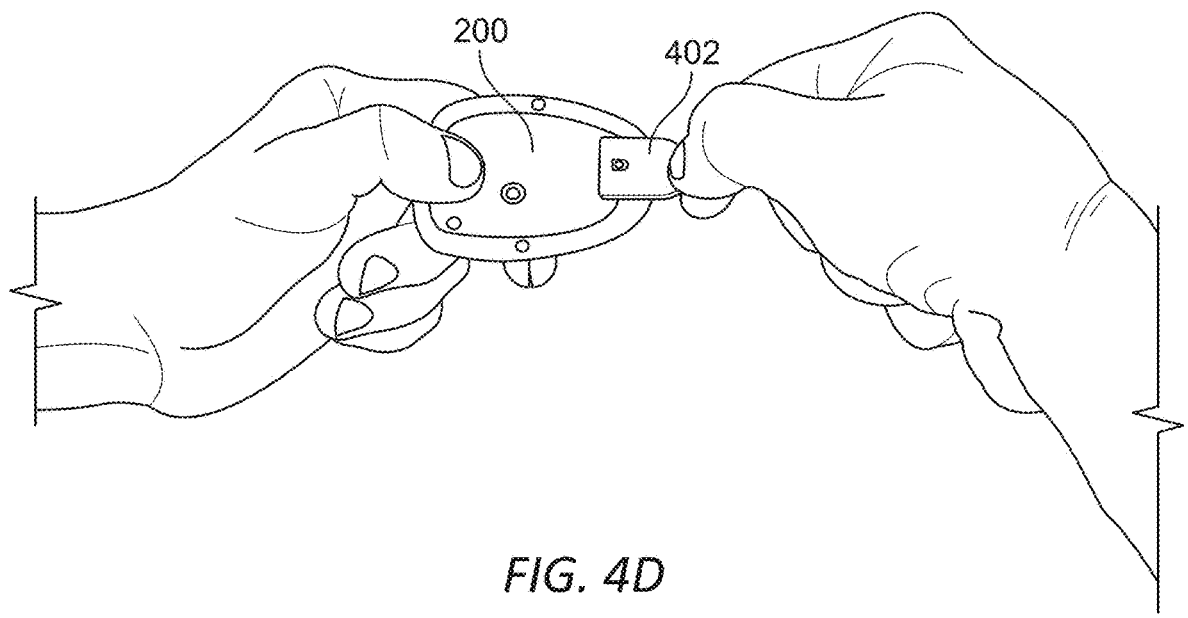
Figure 4E:
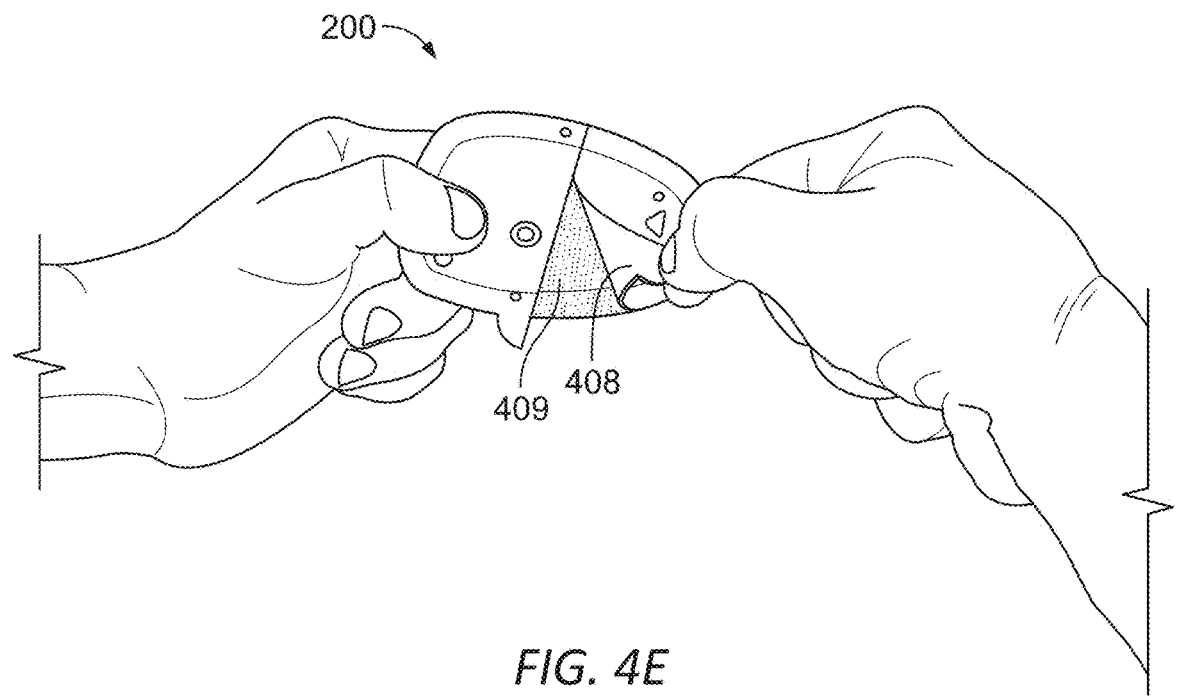
Figure 4F:
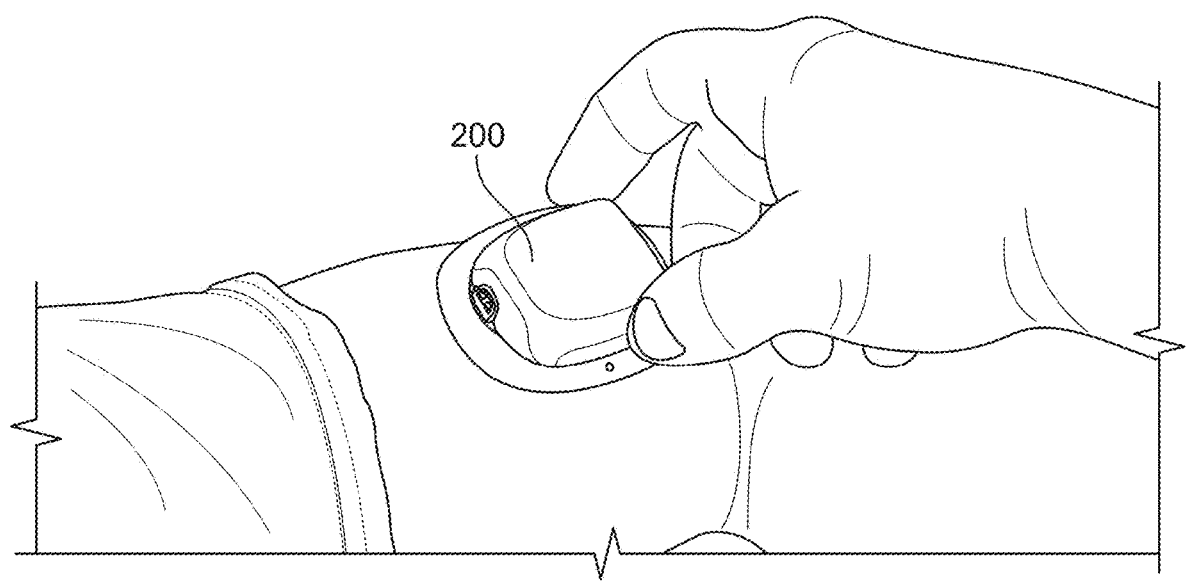
Figure 4G:
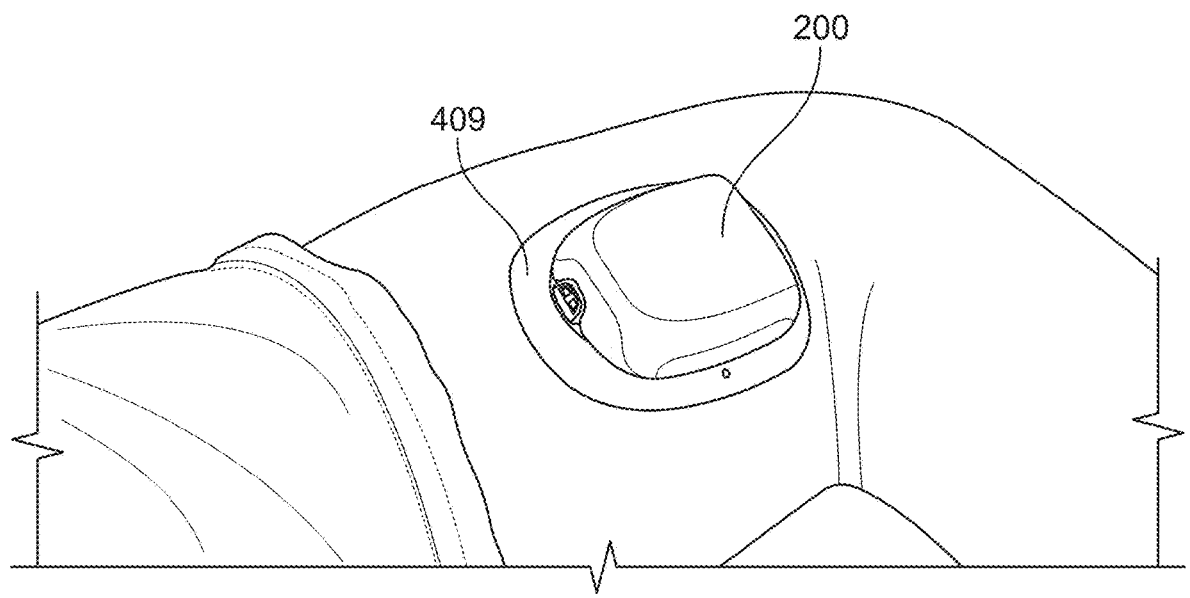

FIG. 4D shows a patient removing cap 402 from the bottom surface of basal pod 200. As previously stated, cap 402 may be of the type shown in FIG. 4D or may be of the type shown in FIGS. 3(A-B), having the integrated fill port guide 304. Basal pod 200 preferably has an adhesive 409 on the bottom surface thereof to facilitate attachment of the basal pod 200 to the body of the patient. In FIG. 4E, the patient removes the backing 408 from the adhesive 409 on the bottom surface of the basal pod 200 and, in FIG. 4F, the patient adheres the basal pod 200 to a convenient location on the patient's body. As shown in FIG. 4F, the patient is positioning the device on the patient's upper arm. The patient may position the basal pod 200 on any convenient location on the patient's body; however, preferably, the basal pod 200 will be oriented such that the user is able to visualize visual status indicator 218. FIG. 4G shows the basal pod 200 deployed on the body of the patient and ready for operation. The patient should have the basal pod 200 in position on his or her body prior to the expiration of the timer initiated by the injection of the liquid drug into reservoir 208.

Upon expiration of the timer, the cannula is inserted into the body of the patient. The cannula may be inserted by a needle driven into the skin of the patient and thereafter withdrawing the needle back into basal pod 200, thereby leaving the cannula deployed into the skin of the patient. Deployment of the cannula may be preceded by activation of audible alert 216, for example, by having audible alert 216 emit one or more short beeps. Audible alert 216 may be activated a second time to emit one or more short beeps to indicate successful deployment of the cannula.

Figure 4H:
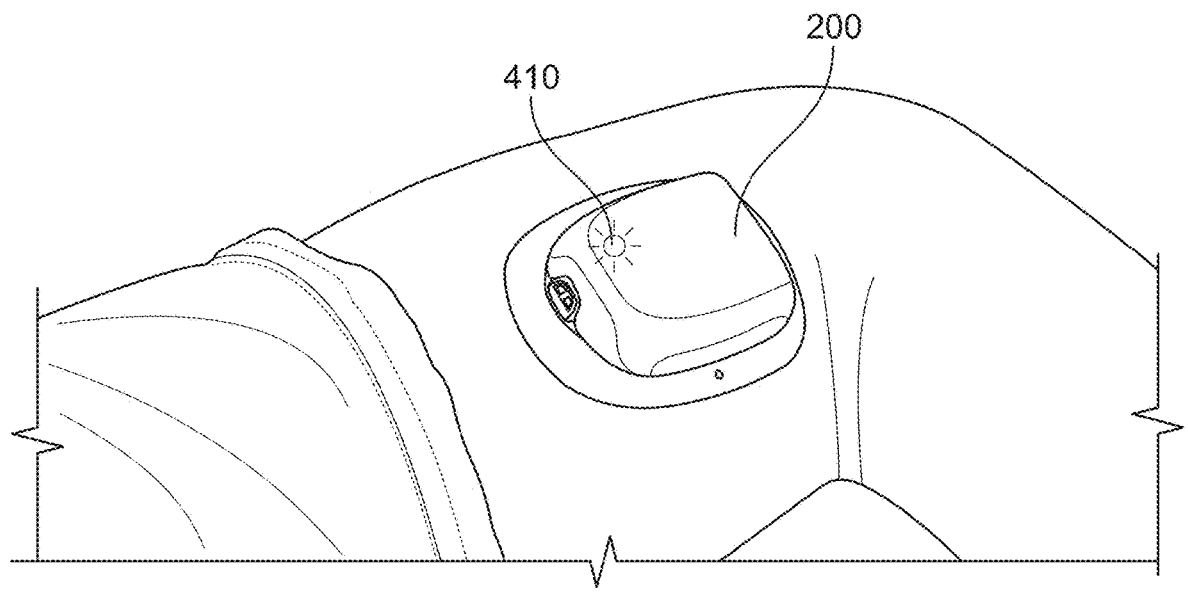

FIG. 4H shows basal pod 200 in an active and functioning state. The active and functioning state of basal pod 200 may be indicated by activation of visual status indicator 218. In a preferred embodiment, for example, visual status indicator 218 may be activated to show a continuous or blinking green indication.

Figure 4I:
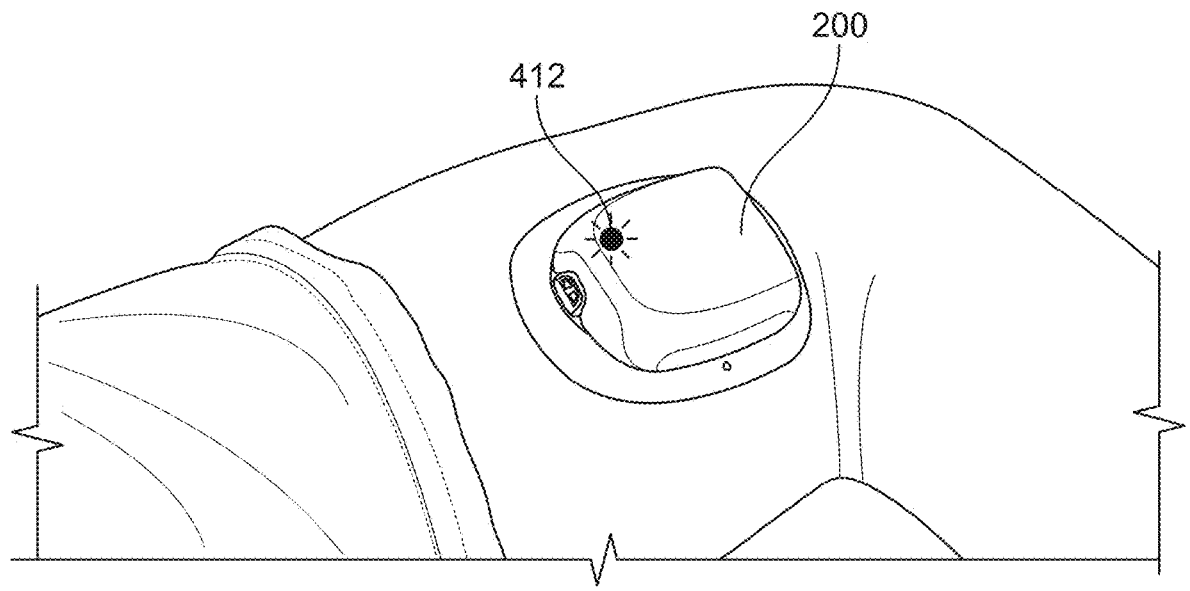

Basal pod 200 will deploy the basal doses of the liquid drug over a period of days under the control of the basal delivery algorithm 206. In a preferred embodiment of the invention, reservoir 208 may contain enough of the liquid drug to last approximately 72 hours. As shown in FIG. 4I, after deployment of the basal doses of the liquid drug over a period of days, basal pod 200 may provide an audible or visual indication that supply of the liquid drug in reservoir 208 is nearly exhausted. In a preferred embodiment of the invention, for example, visual status indicator 218 may be activated to provide a continuous or blinking red or amber indication that the level of the liquid drug remaining in reservoir 208 has reached a critical, predetermined quantity, for example, 20 units, 10 units, 5 units, 0 units, or the like. The audible or visual indication may serve as an indication to the patient that the basal pod 200 may be removed from the patient's body.

Figure 4J:
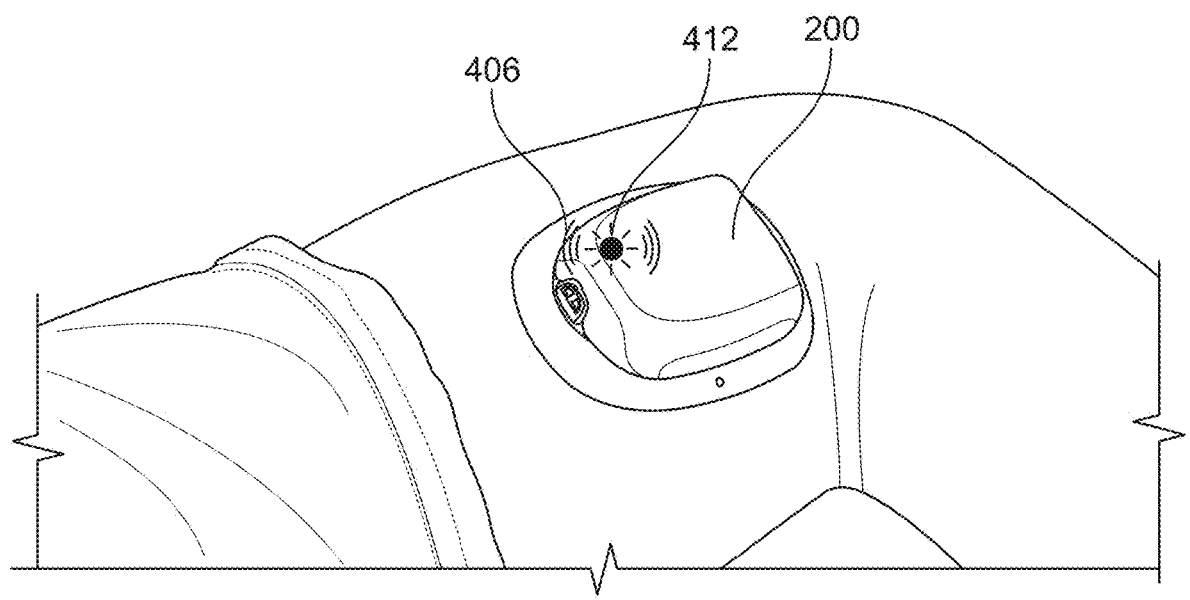

If the patient fails to remove the basal pod 200 after the first audible or visual indication, a further audible or visual indication may be provided, as shown in FIG. 4J. In a preferred embodiment of the invention, the further audible or visual indication may comprise, for example, activating the visual status indicator 218 to provide a blinking red indication and, in addition, activating the audible alert 216 to provide a beep indication. Should the patient still fail to remove the basal pod 200, the audible alert 216 may be further activated to provide a continuous beep, indicating that the basal pod 200 has been deactivated and has ceased delivery of the liquid drug.

Figure 4K:
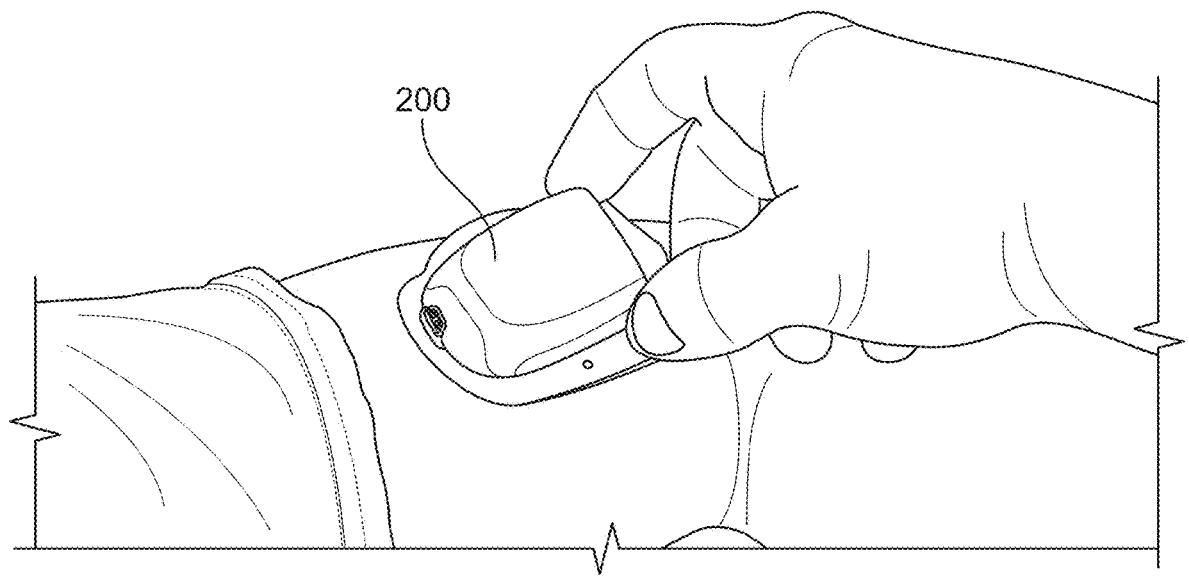

FIG. 4K shows removal of the basal pod 200 from the body of the patient. In certain embodiments of the invention, the cannula may be retracted into the basal pod 200 at the time when the audible or visual indication is provided to the user to remove the basal pod 200. In other embodiments, the cannula may be removed from the skin of the patient as the basal pod 200 is removed from the patient's body.

If, at any time during the deployment of the basal pod 200 on the body of the patient, the basal pod 200 should enter a hazard or error state, an audible and/or visual indication may be provided to the patient. In preferred embodiments of the invention, visual status indicator 218 may be activated to provide a blinking red indication and/or, audible alert 216 may be activated to provide a continuous beeping. Basal pod 200 may enter an error state for a variety of reasons, for example, failure of the cannula to properly deploy, jamming of the reservoir/pump 208, etc. Upon indication of the error state, the basal pod 200 should immediately be removed from the patient's body.

Figure 4L:
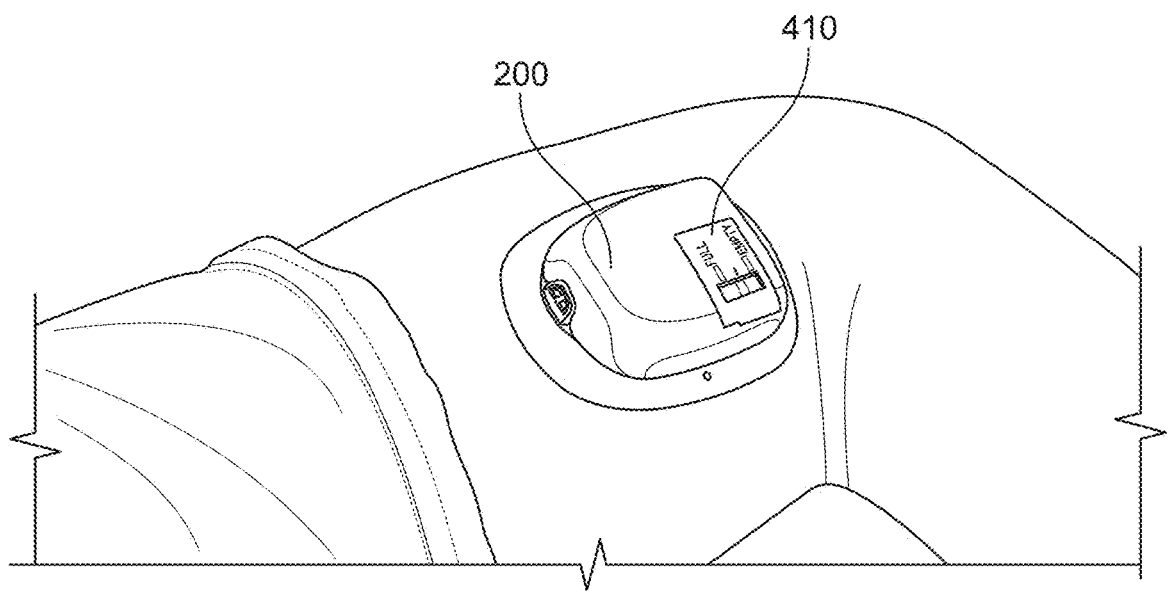
Figure 5:
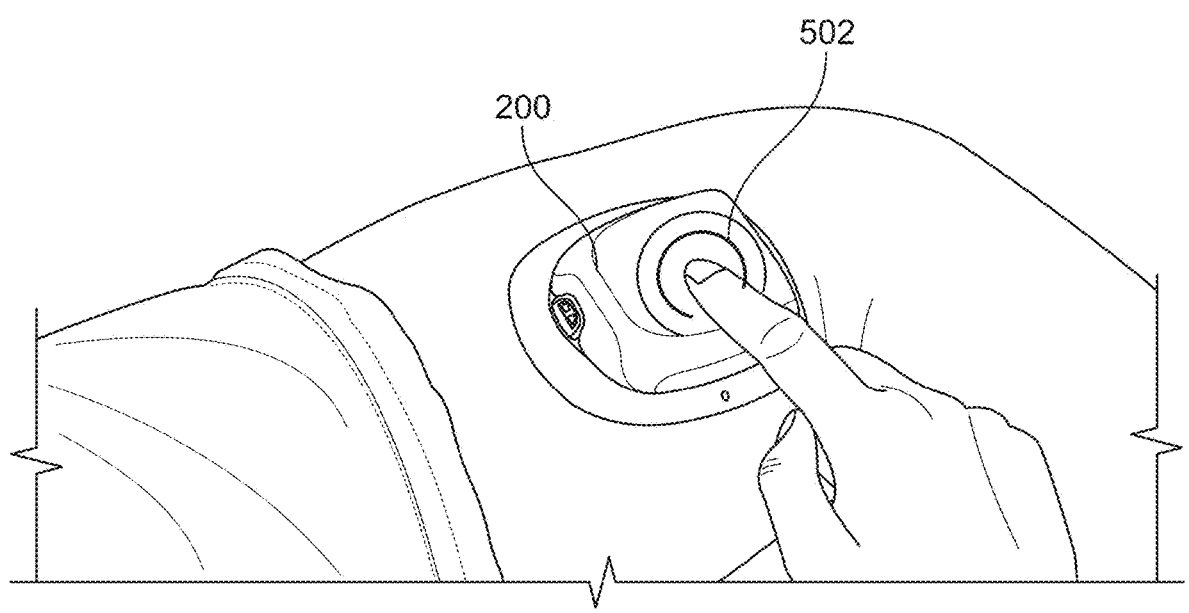
FIG. 5 shows operation of a second embodiment of the device.

As shown in FIG. 4L, the first embodiment of the invention may optionally be provided with a window or indicator 410 of the fill status of the reservoir 408. As shown in FIG. 4L, the status indicator 410 is provided in the form of a gauge akin to a gas gauge in a car showing the level of the reservoir between an empty state and a full state. In other aspects of the invention, any type of indicator 410 indicating that the fill status of the reservoir 208 may be provided.

A second embodiment of the invention is provided which is similar to the first embodiment with the exception that certain aspects of the operation of the basal pod 200 may be controlled by the user via a gesture or series of gestures. The gestures may comprise, for example, tapping on the housing 100 of the basal pod 200. In this embodiment, basal pod 200 may be provided with gesture sensor 220, shown in FIG. 2, which may be, for example, an accelerometer or any other device or sensor capable of detecting contact between the finger of the patient and the housing 100 of the basal pod 200.

In this embodiment of the invention, the insertion of the cannula into the skin of the patient, instead of being initiated by the expiration of the timer, is initiated by a gesture of the patient after the basal pod 200 has been affixed to the body of the patient. In preferred embodiments, the gesture may be, for example, a "double tapping" by the fingertip of the patient on the housing 100 of the basal pod 200, although any gesture could be used. The gesture, as sensed by gesture sensor 220, will cause basal delivery algorithm 206 to initiate a short timer, for example, 10 seconds, the expiration of which will trigger the deployment of the cannula into the skin of the patient.

Additionally, in the second embodiment of the invention, the patient may provide a gesture on the housing 100 of the basal pod 200 to cause an audible alert to cease. For example, alerts indicating the end-of-life of the basal pod 200 or that an error condition exists within the basal pod 200 may be silenced by a gesture from the patient. Additionally, the patient may also provide the patient gesture to eliminate any visual status indicators. For example, the patient may be annoyed by the blinking green light indicating a ready and operating status of the basal pod 200, particularly at night. The patient may provide the patient gesture to cause visual status indicator 218 to be deactivated. In certain embodiments of the invention, the visual status indicator 218 may be reactivated after a predetermined period of time or upon sensing an additional patient gesture.

Gesture sensor 220 may work in conjunction with visual status indicator 218 and/or audible alert 216. For example, when visual status indicator is a certain solid or intermittent color, for example solid yellow, then gesture indicator 220 may be awaiting a gesture (e.g., double tap on the housing), which will cause a certain action (e.g., insertion of the cannula through the patient's skin). Alternatively, when visual status indictor is a different color such as solid red, and/or audible alert 116 is emitting a solid or intermittent beeping alarm, then gesture indicator 220 may cause a different action to occur upon receipt of a gesture from the patient (e.g., double tap on the housing). In this manner, a single, easy-to-remember gesture may cause basal pod 200 to carry out different actions (e.g., insert a needle, begin delivery of basal insulin, pause delivery of basal insulin, or stop a visual status or audible alarm), and the particular color of visual status indicator 218 or sound emitting from audible alert 216 may inform the user what action will result upon performing a gesture (e.g., double tapping the housing of basal pod 200) as sensed by gesture sensor 220. Gesture sensor 220 may sense multiple gestures, each of which may cause a different action to result. For example, tapping twice on the housing of the basal pod 200 while an alarm is sounding may cause the alarm to stop for 10 minutes; and tapping four times on the housing may cause the alarm to stop permanently.

In all other aspects, operation of the second embodiment of the invention is identical to the operation of the first embodiment of the invention.

In a third embodiment of the invention, the basal pod 200 is in wireless communication with the status device 250, as shown in FIG. 2. The basal pod 200 is provided with communication interface 214 which may communicate with communication interface 252 of status device 250 via communication link 240. In preferred embodiments of the invention, the communication link 240 is a Bluetooth connection; however, any other wireless communication protocol may be utilized. Status application 256 is stored in memory 254 of status device 250 and executed by processor 252. Status application 256 may utilize the native user interface 258 of status device 250, for example, the touch-sensitive screen of a smartphone. In preferred embodiments, status device 250 may be, for example, a smartphone, a computing tablet or smartwatch, or any other mobile computing device capable of executing status application 256 and interfacing via the wireless communication link 240 with the basal pod 200.

Status application 256 may provide limited control of the basal pod 200 and also may be configured to provide status feedback to the user regarding the operation state of the basal pod 200, as well as provide instructions for the use of the basal pod 200.

Figure 6A:
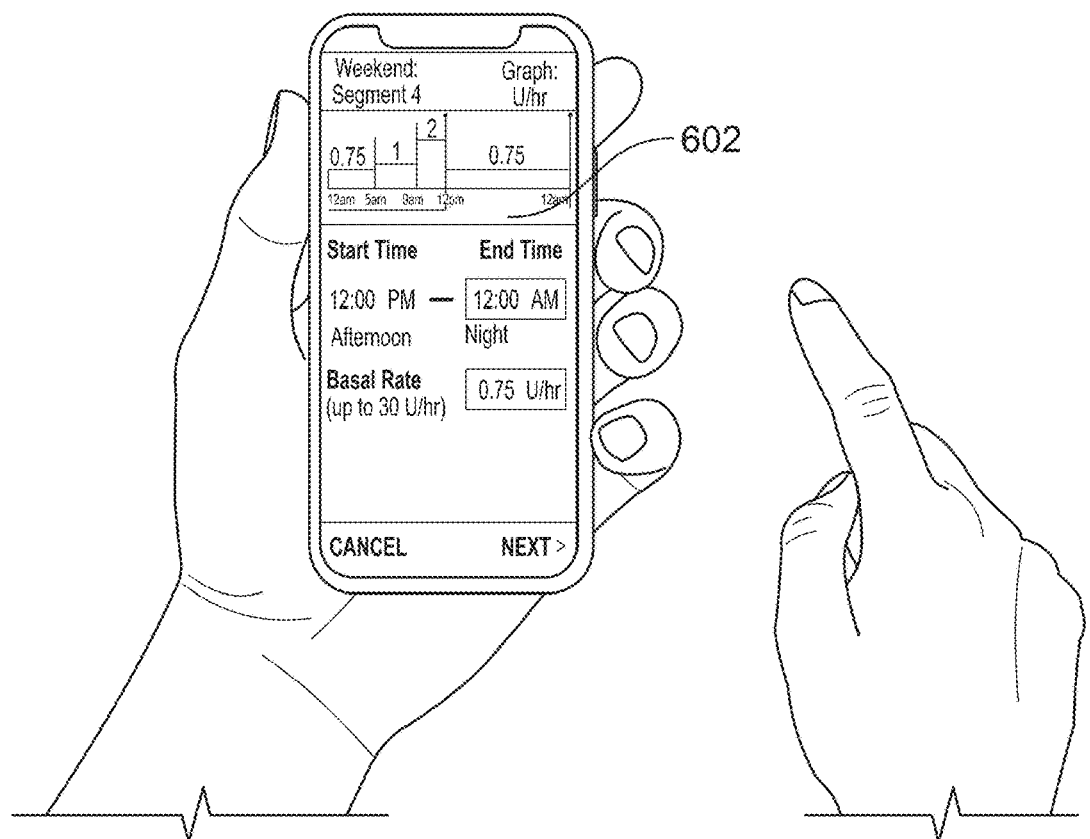
FIGS. 6A-6E show operation of a third embodiment of the device which utilizes a personal computing device executing an application for providing limited control of the device and feedback to the user.

FIG. 6A shows a feature of status application 256 which allows a healthcare professional to establish appropriate preset basal rates via the status application 256. In certain embodiments of the invention, status application 256 may prevent a user from changing the preset basal rates via a password which is known only to the healthcare professional. In alternate embodiments, the healthcare professional may run a special version of status application 256 which allows altering the preset basal rates. In other embodiments of the invention, the user may be able to alter the preset basal rates under the direction of the healthcare professional.

Figure 6B:
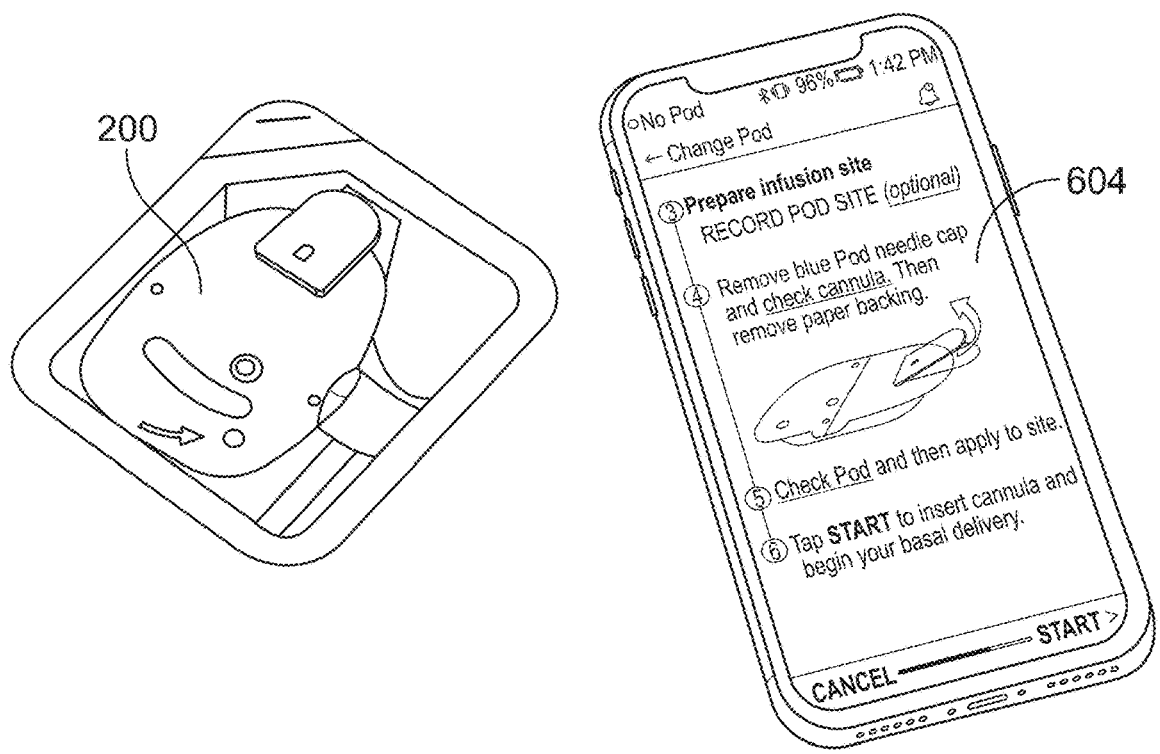
Figure 6C:
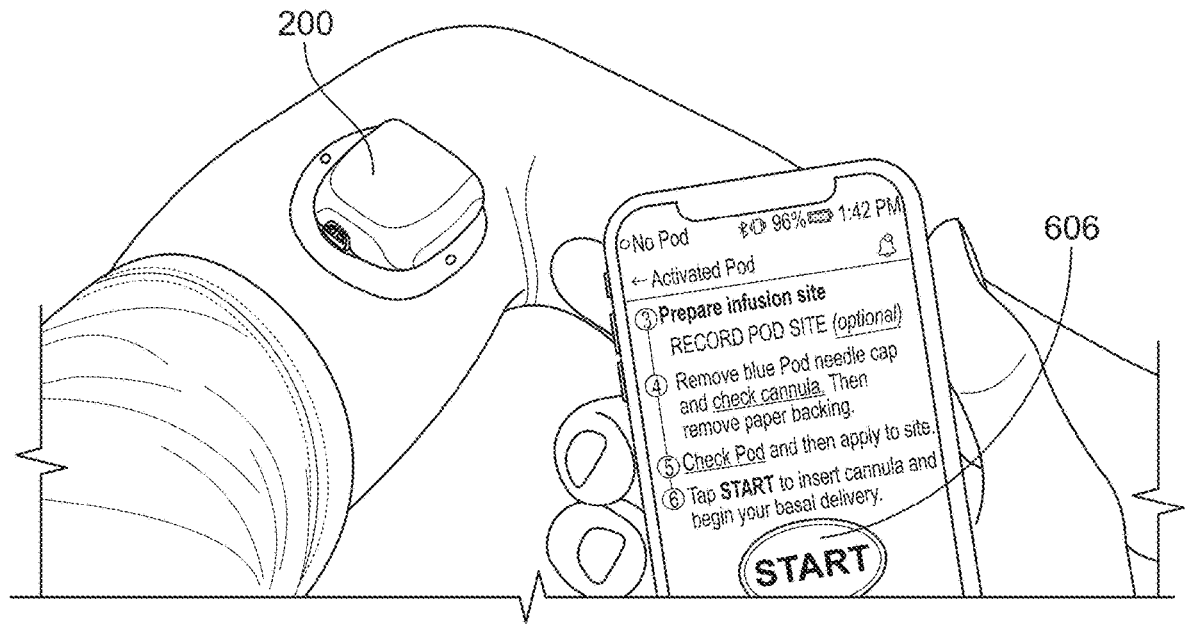
Figure 6D:
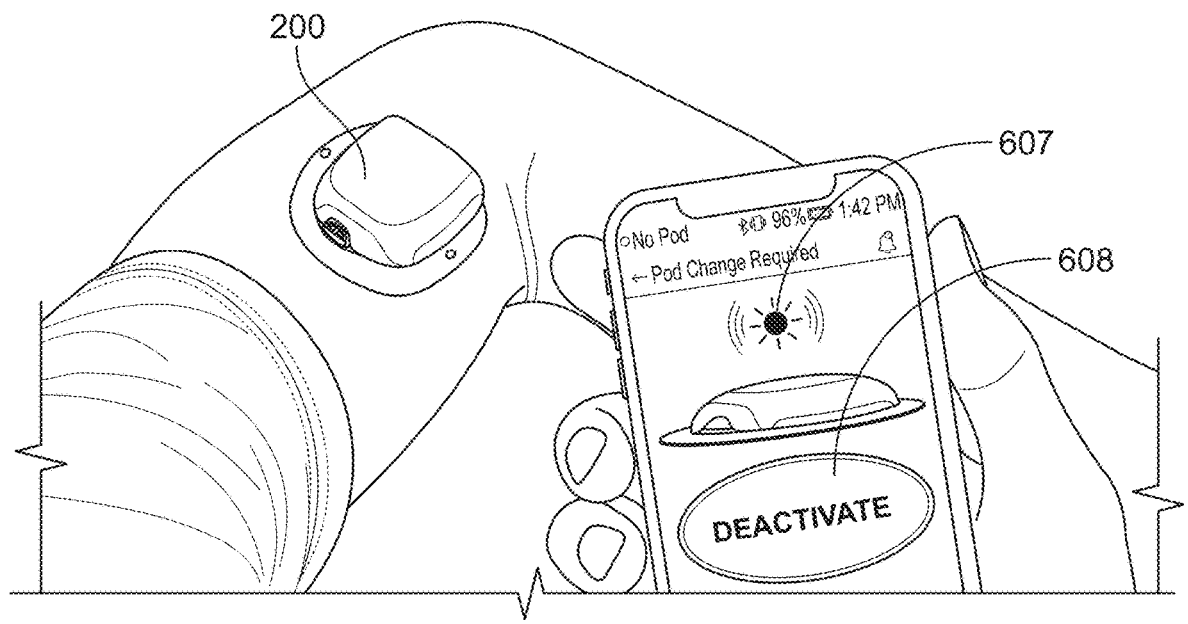

FIG. 6B shows one aspect of status application 256 in which step-by-step instructions are provided to the patient for the deployment and use of the basal pod 200. In FIG. 6C, status application 256 provides a button, in this case labeled "START", in line with the instructions that, when pressed, initiates deployment of the cannula. Likewise, as shown in FIG. 6D, when the basal pod 200 has reached its end-of-life, that is, the basal liquid drug within reservoir 208 has been exhausted, the status application 256 will notify the user via an audible alert 607. The audible alert may be in a form of an alert which may be played through the speakers of the mobile computing device which may be, for example, a single instance of a ringtone provided by the mobile computing device. In addition, a visual alert may be provided which may be in the form, for example, of a banner displayed on the user interface 258 of status device 250, similar to a banner which may be displayed when the user receives an email or text message. Additionally, a "DEACTIVATE" button 608 is provided which, when pressed by the patient, shuts down operation of the basal pod 200. Thereafter, the basal pod 200 may be removed from the patient's body. In the event that the patient fails to deactivate the basal pod 200 using button 608, the audible alert may be repeated periodically until acknowledged by the patient. In this embodiment, the audible and visual alerts on the basal pod 200 may be activated in addition to the audible and visual alerts on status device 250 such as to alert the patient in the case wherein the patient may be separated from his or her mobile computing device.

Figure 6E:
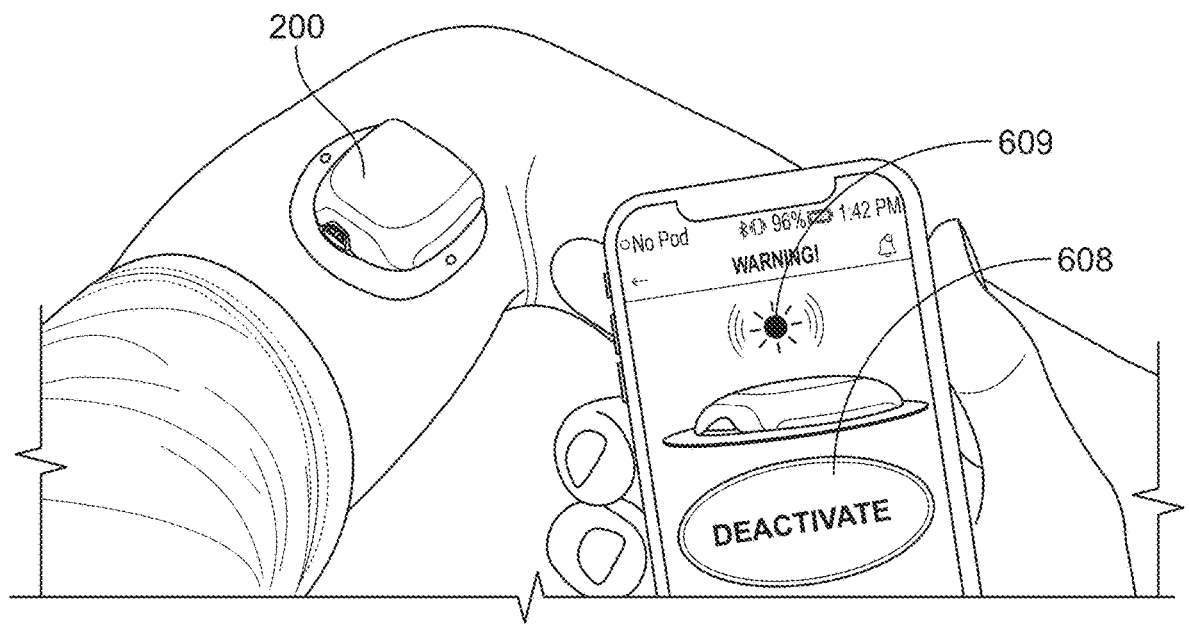

FIG. 6E shows a page of status application 256 which may be displayed in the event of a hazard or error condition arising in the basal pod 200, as previously discussed. As with the end-of-life notifications shown in FIG. 6D, an audible and/or visual alert may be activated on the mobile computing device. In this case, the audible alert may repeat periodically to indicate a more urgent condition requiring the attention of the patient. Status application 256 provides button 610 which may be selected to deactivate the basal pod 200, after which the basal pod 200 may be removed from the patient's body. As with the status alerts shown in FIG. 6D, the warning alerts shown in FIG. 6E may also be activated on the basal pod 200 to alert the patient in the case wherein the patient may be separated from his or her mobile computing device. In the event that the patient fails to acknowledge the alerts, the basal pod 200 may automatically deactivate itself to prevent harm or injury to the patient.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable micro-dosing drug delivery device comprising:

a processor;
software, for execution by the processor, the software comprising a basal delivery algorithm for directing delivery of a basal dose of a liquid drug to a wearer of the device;
a cannula, for interfacing a device with the wearer, wherein the software directs the processor to control insertion of the cannula into the wearer and the insertion of the cannula into the wearer occurs automatically under control of the software after the device has been placed on a body portion of the wearer;
an audible alert component; and
a visual alert component.

2. The drug delivery device of claim 1 wherein the visual alert component comprises a multi-colored LED.

3. The drug delivery device of claim 1:
wherein insertion of the cannula is accompanied by an audible indication via the audible alert component.

4. The drug delivery device of claim 3, further comprising:
a reservoir; and
a fill port coupled to the reservoir;
wherein the liquid drug is introduced into the reservoir via the fill port; and
wherein filling of the reservoir with the liquid drug initiates a timer, wherein an expiration of the timer causes the software to direct the processor to automatically initiate insertion of the cannula into the wearer of the device.

5. The drug delivery device of claim 2 wherein the device provides a visual indication via the visual alert component that the device is operational and ready to deliver the liquid drug to the wearer.

6. The drug delivery device of claim 5 when the visual indication is a continuous or blinking green indication from the multi-colored LED.

7. The drug delivery device of claim 2 wherein the processor detects an error condition and further wherein the device provides a visual indication via the visual alert component of the error condition.

8. The drug delivery device of claim 7 wherein the visual indication of the error condition comprises a continuous or blinking red or amber indication from the multi-colored LED.

9. The drug delivery device of claim 8 wherein the visual indication of the error condition is accompanied by an audible indication of the error condition.

10. The drug delivery device of claim 9 wherein the audible indication of the error condition comprises a continuous or repeating beeping sound from the audible alert component.

11. The drug delivery device of claim 2 further comprising:
a gesture sensor, coupled to the processor to provide an indication of a gesture from the wearer.

12. The device of claim 11 wherein the gesture received from the wearer causes the device to perform an operation, the operation performed being dependent on a current operational state of the device.

13. The device of claim 12 wherein the operational state of the device is indicated to the wearer via the audible alert component or the visual alert component.

14. The drug delivery device of claim 11 wherein the gesture sensor comprises an accelerometer capable of sensing a gesture comprising a pattern of taps from a finger of the wearer on a housing of the device.

15. The drug delivery device of claim 12 wherein the operation performed is insertion of the cannula.

16. The drug delivery device of claim 12 wherein the operation performed is the audible alert component or the visual alert component.

17. The drug delivery device of claim 1 further comprising:
a wireless communications interface.

18. The drug delivery device of claim 17 wherein the device communicates with a status application executing on a status device via the wireless communications interface.

19. The drug delivery device of claim 18 wherein the device provides information to the status application regarding its current operational condition.

20. The drug delivery device of claim 19 wherein a wearer of the device initiates insertion of the cannula via an input to the status application.

21. The drug delivery device of claim 19 wherein where the device initiates the de-activation of the device via an input to the status application.

22. The drug delivery device of claim 19 wherein basal delivery rates for the liquid drug are set via an input to the status application.

23. The method of claim 22 wherein an audible indication is provided accompanying insertion of a cannula interfacing the wearable basal drug delivery device to the wearer.

24. The method of claim 22 wherein a visual indication is provided indicating a current operational state of the wearable basal drug delivery device.

25. The method of claim 22 further comprising:
receiving a gesture from the wearer of the wearable basal drug delivery device via a gesture sensor, the gesture comprising a tapping on a housing of the wearable drug delivery device.

26. The method of claim 25 wherein the gesture received from the wearer causes the device to perform an operation, the operation performed being dependent on a current operational state of the device.

27. The device of claim 26 wherein the operational state of the device is indicated to the wearer via the audible alert component or the visual alert component.

28. The method of claim 26 wherein the operation performed is insertion of a cannula interfacing the wearable drug delivery device to the wearer.

29. The method of claim 26 wherein the operation performed is deactivation of the audible or visual indications.

30. The method of claim 26 wherein the operation performed is deactivation of the device.

31. The method of claim 22, further comprising:
providing a wireless communications interface for communicating with a status application on a status device;
providing operational status of the device to the status application; and
receiving input from the wearer of the device via the status application.

32. The drug delivery device of claim 1 wherein the basal delivery algorithm dispenses basal doses of the liquid drug in accordance with pre-programmed basal rates.

33. A starter kit comprising one or more quantities of the devices of claim 24 having different pre-programmed basal rates.

34. A method for providing status information to and receiving input from a wearer of a wearable basal drug delivery device comprising:
providing audible indications via an audible alert component;

providing visual indications via a visual alert component; and directing, by software on the wearable basal drug delivery device, a cannula configured to interface the device with the wearer, to control insertion of the cannula into the wearer, wherein the insertion of the cannula into the wearer occurs automatically under control of the software after the device has been placed on a body portion of the wearer.

* * * * *